(12) United States Patent
Buchanan et al.

(10) Patent No.: US 6,407,279 B1
(45) Date of Patent: Jun. 18, 2002

(54) INTEGRATED PROCESS FOR PREPARING DIALKYL CARBONATES AND DIOLS

(75) Inventors: J. Scott Buchanan, Trenton; Zhaozhong Jiang, Thorofare; Jocelyn A. Kowalski, Sewell, all of NJ (US); Jose G. Santiesteban, West Chester, PA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 09/444,231

(22) Filed: Nov. 19, 1999

(51) Int. Cl.[7] ............................................. C07C 69/96
(52) U.S. Cl. ...................................... 558/277; 558/260
(58) Field of Search .......................................... 558/277

(56) References Cited

U.S. PATENT DOCUMENTS

| | | | |
|---|---|---|---|
| 2,773,070 A | 12/1956 | Lichtenwalter et al. | 549/230 |
| 3,748,345 A | 7/1973 | DePasquale et al. | 547/230 |
| 4,233,221 A | 11/1980 | Raines et al. | 549/230 |
| 4,314,945 A | 2/1982 | McMullen et al. | 549/230 |
| 4,519,875 A | 5/1985 | Becker et al. | |
| 4,661,609 A | 4/1987 | Knifton | 558/277 |
| 4,691,041 A | 9/1987 | Duranleau et al. | 558/277 |
| 4,734,518 A | 3/1988 | Knifton | 558/277 |
| 4,786,741 A | 11/1988 | Sachs | 549/230 |
| 4,851,555 A | 7/1989 | Weinstein | 549/518 |
| 4,877,886 A | 10/1989 | Ream | 549/230 |
| 4,931,571 A | 6/1990 | Weinstein | 549/230 |
| 4,952,542 A | 8/1990 | Ream | 502/27 |
| 5,138,073 A | 8/1992 | Harvey | 549/230 |
| 5,179,214 A | 1/1993 | Marquis et al. | 549/230 |
| 5,183,920 A | 2/1993 | Myers | 558/277 |
| 5,214,182 A | 5/1993 | Knifton | 558/277 |
| 5,218,135 A | 6/1993 | Buysch et al. | 558/277 |
| 5,231,212 A | 7/1993 | Buysch et al. | 558/277 |
| 5,391,767 A | 2/1995 | Mais et al. | 549/229 |
| 5,498,743 A | 3/1996 | Shih et al. | 558/277 |
| 5,763,691 A | 6/1998 | Kawabe et al. | 568/867 |
| 5,847,189 A | 12/1998 | Tojo et al. | |

FOREIGN PATENT DOCUMENTS

| | | | | |
|---|---|---|---|---|
| DE | 4138755 | * | 5/1993 | 558/277 |
| EP | 0543234 | * | 5/1993 | 558/277 |
| JP | 4-230243 | * | 8/1992 | 558/277 |
| JP | 6-336463 | * | 12/1994 | 558/277 |

OTHER PUBLICATIONS

Wang, S.H., "The Coproduction of Dimethyl Carbonate and Ethylene Glycol by Transesterification", PEP Review No. 92–1–1 (SRI International) pp. 1–35 (May 1993).

\* cited by examiner

Primary Examiner—Floyd D. Higel
Assistant Examiner—Ebenezer Sackey

(57) ABSTRACT

An integrated process for the production of a dialkyl carbonate and a diol from an alkylene oxide, carbon dioxide and an aliphatic monohydric alcohol is described in which an alkylene oxide is first reacted with carbon dioxide in the presence of a carbonation catalyst to provide a corresponding cyclic carbonate and impurities and the cyclic carbonate, which contains the impurities, is then reacted with an aliphatic monohydric alcohol in the presence of a transesterification catalyst to provide a corresponding dialkyl carbonate and diol.

12 Claims, 1 Drawing Sheet

INTEGRATED PROCESS FOR PREPARING DIALKYL CARBONATES AND DIOLS

BACKGROUND OF THE INVENTION

Figure 1:
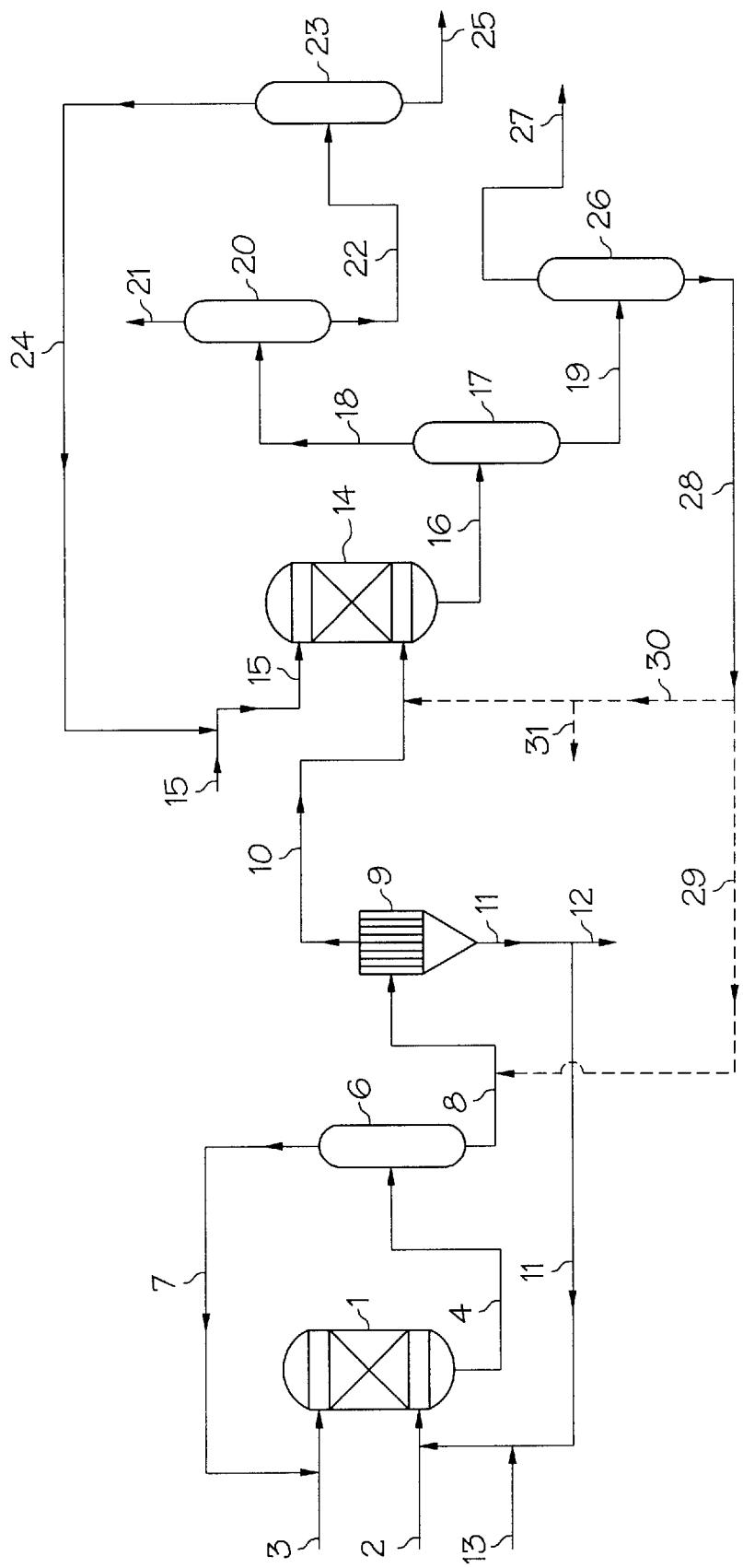

This invention relates to a process for preparing dialkyl carbonates and diols. More specifically the present invention relates to an integrated process for preparing dialkyl carbonates and diols from alkylene oxides, carbon dioxide and alcohols.

Dialkyl carbonates are important intermediates for the synthesis of fine chemicals, pharmaceuticals and plastics and are useful as synthetic lubricants, solvents, plasticizers and monomers for organic glass and various polymers, including polycarbonate, a polymer known for its wide range of uses based upon its characteristics of transparency, shock resistance and processability.

One method for the production of polycarbonate resin employs phosgene and bisphenol-A as starting materials. However, this method has numerous drawbacks, including the production of corrosive by-products and safety concerns attributable to the use of the highly toxic phosgene. As such, polycarbonate manufacturers have developed non-phosgene methods for polycarbonate production, which use diphenyl carbonate and bisphenol-A as starting materials.

Dimethyl carbonate has a low toxicity and can also be used to replace toxic intermediates, such as phosgene and dimethyl sulphate, in many reactions, such as the preparation of urethanes and isocyanates, the quaterniation of amines and the methylation of phenol or naphthols. Moreover, it is not corrosive and it will not produce environmentally damaging by-products. Dimethyl carbonate is also a valuable commercial product finding utility as an organic solvent, an additive for fuels, and in the production of other alkyl and aryl carbonates.

Dimethyl carbonate, as well as other dialkyl carbonates, have traditionally been produced by reacting alcohols with phosgene. These methods have the same problems as methods that use phosgene and bisphenol-A, i.e. the problems of handling phosgene and disposing of phosgene waste materials. Thus, there is a need for commercially viable non-phosgene methods for the production of dimethyl carbonate, as well as other dialkyl carbonates.

Non-phosgene methods that have been proposed for producing dialkyl carbonates include the transesterification reaction of alcohols and cyclic carbonates. Most of the proposed methods relate to the use of various catalysts for that reaction. Examples of such proposed catalysts include alkali metals or basic compounds containing alkali metals; tertiary aliphatic amines; thallium compounds; tin alkoxides; alkoxides of zinc, aluminum and titanium; a mixture of a Lewis acid and a nitrogen-containing organic base; phosphine compounds; quaternary phosphonium salts; cyclic amidines; compounds of zirconium, titanium and tin; a quaternary ammonium group-containing strongly basic anion-exchange solid material; a solid catalyst selected from the group consisting of a tertiary amine-or quaternary ammonium group-containing ion-exchange resin, a strongly acidic or a weakly acidic ion-exchange resin, a mixture of an alkali metal with silica, a silicate of an alkaline earth metal and an ammonium ion-exchanged zeolite; and a homogeneous catalyst selected from the group consisting of tertiary phosphine, tertiary arsine, tertiary stibine, a divalent sulfur compound and a selenium compound.

With respect to the method for carrying out the above-mentioned transesterification reaction between a cyclic carbonate and an alcohol, the proposed methods generally rely upon using commercial grade reactants (i.e., the cyclic carbonate and the alcohol) having a relatively high purity to achieve adequate reaction rate, yield and selectivity to the desired dialkyl carbonates and diols, as discussed more fully below.

It is known to react alkylene oxides with $CO_2$ in the presence of catalysts to give cyclic carbonates. The proposed methods for this reaction again mostly relate to the development of various catalysts. Examples of such proposed catalysts include alkali metal halides; ammonium, phosphonium or sulphonium halide carbonates; a combination of protic compounds, such as alcohols, and nitrogen-containing bases; arsonium halides; tertiary phosphines with alcohols; and alkali metal transfer catalysts with crown ethers and other ligands.

Although some of these proposed methods for producing cyclic carbonates will provide relatively high yields and selectivity to the desired cyclic carbonate, inevitably a significant amount of glycols are produced as by-products of the reaction between the alkylene oxides and $CO_2$. For example, the reaction between ethylene oxide and $CO_2$ to produce ethylene carbonate will inevitably produce a certain amount of ethylene glycol and higher molecular weight glycols, e.g. di- and tri-ethylene glycol. It is generally believed that the presence of these glycol impurities contained in the cyclic carbonate will adversely affect the transesterification reaction between the cyclic carbonate and an alcohol, since certain glycols, e.g. ethylene glycol, will typically unfavorably affect the equilibrium of the reaction, thereby lowering yield or possibly selectivity for the desired products. In addition, the glycols have hydroxyl (—OH) groups which would be expected to compete with the alcohol in reacting with the cyclic carbonate, forming unwanted heavier carbonates and other undesired species. Moreover, since the glycol impurities, e.g. ethylene glycol and triethylene glycol, are generally hygroscopic in nature, the cyclic carbonate containing these glycol impurities will tend to absorb water during storage. When water is present in sufficient quantity in the reaction mixture, hydrolysis takes place simultaneously with the transesterification reaction, resulting in a decrease in the selectivity for the dialkyl carbonate. Thus, in order to avoid the problems associated with the glycol impurities, the proposed methods for producing dialkyl carbonates from a cyclic carbonate have required a relatively high purity cyclic carbonate.

In order to provide a high purity commercial grade cyclic carbonate, e.g. ethylene carbonate, useful as a reactant in connection with the proposed methods discussed above, difficult separations have to be performed to achieve the requisite cyclic carbonate purity, resulting in increased operating and capital costs. Typically, the purification process for a cyclic carbonate, e.g. ethylene carbonate, produced by reacting an alkylene oxide with $CO_2$, will include the following: (1) flashing the carbonation reactor effluent to remove the light ends; (2) passing the remaining liquid through one or more evaporators to remove and recycle catalyst, and to remove heavies; (3) distilling the crude product stream containing the cyclic carbonate and mono- and poly-glycols in a first vacuum distillation column, containing between about 8 and 50 trays, to remove the majority of the mono- and poly-glycols; and (4) distilling the purified cyclic carbonate stream in a finishing vacuum distillation column, containing between about 8 and 50 trays, to remove remaining polyglycols and other heavies and to provide a high purity cyclic carbonate.

There are significant capital and operating costs associated with the two vacuum distillation columns needed to provide a high purity cyclic carbonate. Moreover, a significant amount of the cyclic carbonate is generally lost as a result of the purification process. For example, in the case of ethylene carbonate, an azeotrope is formed in the first vacuum distillation column, which can contain about 91% ethylene glycol and 9% ethylene carbonate, depending upon the pressure in the column, so that a significant amount of ethylene carbonate is removed with the ethylene glycol. Moreover, depending upon the operating conditions of the distillation columns, and specifically the high temperatures associated with full reboiled columns, a certain amount of decomposition of the cyclic carbonate can occur resulting in additional losses.

As can be understood from the above, no proposal has heretofore been made with respect to an integrated process for producing a dialkyl carbonate and a diol from an alkylene oxide, carbon dioxide and an alcohol, having high productivity, which first reacts an alkylene oxide with carbon dioxide in the presence of a carbonation catalyst to provide a cyclic carbonate, which contains by-product impurities, and then uses the cyclic carbonate containing the impurities as a feedstock for a second transesterification reaction.

SUMMARY OF THE INVENTION

According to the present invention, it has now been found that a dialkyl carbonate and a diol, and more specifically dimethyl carbonate and ethylene glycol, can be prepared according to an integrated process having high productivity, by:

reacting an alkylene oxide (ethylene oxide in the case of dimethyl carbonate and ethylene glycol) with carbon dioxide in the presence of a carbonation catalyst in a first reaction zone to provide a crude cyclic carbonate stream comprising a cyclic carbonate (ethylene carbonate in the case of dimethyl carbonate and ethylene glycol) and impurities (e.g. ethylene glycol and higher molecular weight glycols in the case of dimethyl carbonate and ethylene glycol);

directing the crude cyclic carbonate stream to a second reaction zone;

reacting the cyclic carbonate (e.g. ethylene carbonate) with an aliphatic monohydric alcohol (methanol in the case of dimethyl carbonate and ethylene glycol), in the second reaction zone in the presence of a transesterification catalyst to provide a crude product stream containing a corresponding dialkyl carbonate (e.g. dimethyl carbonate) and diol (e.g. ethylene glycol); and recovering the dialkyl carbonate and the diol from the crude product stream.

Preferably, the alkylene oxide is of the formula:

 (I)

wherein $R_1$ and $R_2$ independently of one another denote a divalent group represented by the formula —$(CH_2)_m$—, wherein m is an integer from 1 to 3, which is unsubstituted or substituted with at least one substituent selected from the group consisting of $C_1$–$C_{10}$ alkyl group and a $C_6$–$C_{10}$ aryl group, wherein $R_1$ and $R_2$ can share the same substituent; and said aliphatic monohydric alcohol is of the formula:

$R_3$—OH (II)

wherein $R_3$ is a monovalent aliphatic $C_1$–$C_{12}$ hydrocarbon group which is unsubstituted or substituted with at least one substituent selected from the group consisting of a $C_1$–$C_{10}$ alkyl group and a $C_6$–$C_{10}$ aryl group.

The present invention provides the advantage of continuously producing dialkyl carbonates and diols, such as dimethyl carbonate and ethylene glycol, with relatively high yield and selectivity to the desired dialkyl carbonate and diol, and obtaining the productivity and economic benefits associated with integrating the carbonation and transesterification processes.

Additional objects, advantages and novel features of the invention will be set forth in part in the description and examples which follow, and in part will become apparent to those skilled in the art upon examination of the following, or may be learned by practice of the invention. The objects and advantages of the invention may be realized and attained by means of the instrumentalities and combinations particularly pointed out in the appended claims.

DETAILED DESCRIPTION OF PREFERRED EMBODIMENTS

The present invention is a continuous integrated process for preparing dialkyl carbonates and diols from alkylene oxides, carbon dioxide and aliphatic monohydric alcohols.

In preparing the dialkyl carbonates and diols, an alkylene oxide is first reacted with $CO_2$ in the presence of a carbonation catalyst to provide a corresponding cyclic carbonate. Preferably, the alkylene oxide is represented by structural formula (I) above. Examples of such alkylene oxides include ethylene oxide, propylene oxide, styrene oxide, trimethylene oxide, cyclohexene oxide, and the like. Of these alkylene oxides, ethylene oxide and propylene oxide are preferably used because of their good availability and high demand end proproducts. Ethylene oxide is most preferably used.

The first carbonation reaction involving this preferred alkylene oxide may be represented by the following:

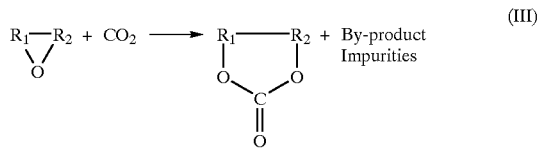 (III)

wherein $R_1$ and $R_2$ independently of one another denote a divalent group represented by the formula —$(CH_2)_m$—, wherein m is an integer from 1 to 3, which is unsubstituted or substituted with at least one substituent selected from the group consisting of $C_1$–$C_{10}$ alkyl group and a $C_6$–$C_{10}$ aryl group, wherein $R_1$ and $R_2$ can share the same substituent.

The carbon dioxide to be employed can contain inert gases, such as nitrogen, hydrogen, carbon monoxide and lower hydrocarbons, and can originate from natural sources or industrial waste gases.

The content and amount of carbon dioxide will depend on the reaction rate, reactor type and specific catalyst used, and is adjusted to maximize the economics of the process. Preferably, the molar ratio of alkylene oxide to carbon dioxide is about 1:1, but an excess of carbon dioxide is also contemplated.

Therefore, according to the invention, the molar ratio of alkylene oxide to carbon dioxide is preferably in the range from about 1:0.9 to 1:15 and more preferably in the range from about 1:1 to 1:3.

The reactants (i.e. alkylene oxide and carbon dioxide) are contacted in the presence of a carbonation catalyst. The carbonation catalyst can typically be any homogeneous catalyst known in the art which provides adequate reaction kinetics. Preferred homogeneous carbonation catalysts include phosphonium halides, arsonium halides, quaternary ammonium halides and alkali halides. The carbonation catalyst can also include heterogeneous catalysts such as, for example, anion exchange resins having quaternary ammonium functional groups or solid support catalysts containing an element of groups IA or IIA of the periodic table, such as those described in application Ser. No. 09/332,725 filed Jun. 14, 1999, which is incorporated herein by reference.

The specific catalyst is chosen to optimize the economics of the overall integrated process and will depend upon the particular alkylene oxide being reacted and the reaction conditions. For example, it is contemplated that tetraethyl ammonium bromide and potassium iodide are particularly effective for the synthesis of ethylene carbonate. The weight ratio of catalyst to alkylene oxide is generally about 0.001:1 to 0.05:1, preferably about 0.003:1 to 0.02:1.

The carbonation reaction is preferably carried out in a continuous mode utilizing various reaction configurations, such as a stirred-tank, tubular, fixed or packed-bed reactor, in a single or multiple-reactor configuration, at from about 50° C. up to about 250° C., preferably between about 100° C. up to about 200° C., and at pressures ranging from about atmospheric pressure up to about 14000 Kpa (2000 psi), preferably from about 2000 Kpa ( 300 psi) up to about 9000 Kpa (1300 psi). In the preferred mode of operation, the reactor temperature and pressure are optimized to insure a relatively high conversion and selectivity to the desired cyclic carbonate. A provision for heat removal from the reactor is normally required, since the carbonation reaction is exothermic.

Preferably, the effluent from the carbonation reaction zone is fed into a second carbonation reaction zone that can operate under different conditions or a different configuration to provide a greater overall conversion of the alkylene oxide, preferably greater than 90% overall conversion. Preferably, the second carbonation reaction zone is a separate tubular polishing reactor which operates at from about 50° C. up to about 250° C., preferably between about 100° C. up to about 200° C. and at pressures ranging from about atmospheric up to about 14000 Kpa (2000 psi), preferably from about 2000 Kpa (300 psi) to about 9000 Kpa (1300 psi).

Inevitably, impurities are formed in the carbonation reaction in the form of by-products. Typically, glycols are formed along with the cyclic carbonates, especially if there is water present in the system. For example, by reacting ethylene oxide with $CO_2$ to produce ethylene carbonate, inevitably ethylene glycol and some higher molecular weight glycols are produced.

The carbonation reactor effluent, either from the first carbonation reaction zone or from the second carbonation reaction zone (if used), is preferably subjected to a flash separation to remove the volatiles, such as unreacted $CO_2$ and alkylene oxide. In the case of a homogeneous carbonation catalyst, the carbonation reactor effluent will be fed to a separating apparatus to recover the catalyst for recycle to the carbonation reaction zone(s). Examples of such separating apparatuses include an evaporation type separating apparatus, a crystallization type separating apparatus, an absorption type separating apparatus and a membrane type separating apparatus. A combination of a plurality of different or identical separating apparatuses may be used. An evaporation type separating apparatus is especially preferred.

In one embodiment, an evaporator used to recover the homogeneous carbonation catalyst is surmounted by a packed or trayed column rectifying section, having a condenser and reflux. The vaporous effluent from the evaporator, which contains cyclic carbonate and by-product impurities, rises up through the rectifying section where it is condensed and refluxed back down into the evaporator. The condensate effectively flows countercurrent to the rising vapor and helps to wash additional homogeneous catalyst and unwanted heavies from the rising vapor. The crude cyclic carbonate (containing by-product impurities) is recovered overhead of the evaporator as a liquid. In such a configuration, the operating conditions are controlled to minimize decomposition of the cyclic carbonate and the homogeneous catalyst, but to achieve a relatively high recovery of the homogeneous catalyst. As such, the residence time of the carbonation reactor effluent fed to the evaporator/rectifying section is minimized with the reflux ratio relative to the recovered crude cyclic carbonate typically about 0.1 to 0.7. As a comparison, a typical reboiled distillation column has a reflux ratio in excess of 1. The recovered crude cyclic carbonate under such conditions can have between about 0.5 and 40 wt % by-product impurities.

The use of such an evaporator (having a rectifying section) provides improved removal of the homogeneous catalyst and heavies from the crude cyclic carbonate than a typical evaporator, but avoids the high heat and long liquid residence time of a full reboiled distillation column, which can decompose the cyclic carbonate, and the additional costs and yield penalties associated with such a column.

The effluent from the carbonation reaction is preferably not subjected to any further separation. Thus, the cyclic carbonate and the by-product impurities produced in the carbonation reaction are then fed to the second transesterification reaction zone, where the cyclic carbonate is reacted with an aliphatic monohydric alcohol in the presence of a transesterification catalyst to provide a corresponding dialkyl carbonate and diol.

Preferably, the aliphatic monohydric alcohol is represented by structural formula (II) above and has a boiling point lower than that of the produced diol. The type of an aliphatic monohydric alcohol which can be used in the present invention varies depending on the particular cyclic carbonate produced by the carbonation reaction. Examples of such aliphatic monohydric alcohols include methanol, ethanol, n-propanol, iso-propanol, allyl alcohol, butanol (including isomers of butanol), 3-butene-1-ol, amyl alcohol (isomers), hexyl alcohol (isomers), heptyl alcohol (isomers), octyl alcohol (isomers), nonyl alcohol (isomers), decyl alcohol (isomers), undecyl alcohol (isomers), dodecyl alcohol (isomers), cyclopentanol, cyclohexanol, cycloheptanol, cyclooctanol, methylcyclopentanol (isomers), ethylcyclopentanol (isomers), methylcyclohexanol (isomers), ethylcyclohexanol (isomers), dimethylcyclohexanol (isomers), diethylcyclohexanol (isomers), phenylcyclohexanol (isomers), benzyl alcohol, phenethyl alcohol (isomers), phenylpropanol (isomers), and the like. The above mentioned aliphatic monohydric alcohol may be substituted with at least one substituent, such as a halogen atom, a lower alkoxy group, a cyano group, an alkoxycarbonyl group, an aryloxycarbonyl group, an acyloxy group, a nitro group or the like.

Of these aliphatic monohydric alcohols, an alcohol having 1 to 6 carbon atoms is preferably used. When ethylene carbonate is the cyclic carbonate, an alcohol having 1 to 4 carbon atoms, i.e., methanol, ethanol, propanol (isomers) or butanol (isomers) is preferably used. The method of the present invention can be employed advantageously especially when methanol and ethylene carbonate are used as feedstocks for the transesterification reaction.

According to the present invention, it has now been found that it is unnecessary to purify the cyclic carbonate to achieve relatively high yields and selectivity to the desired dialkyl carbonate and diol, resulting in significant economic benefits and advantage due to the elimination of the purification steps, e.g. two vacuum distillation columns, previously thought necessary. In addition to lower operating and capital costs associated with e liminating the purification steps, a yield benefit is realized by eliminating losses of cyclic carbonate attributable to the purification steps. As such, an integrated process is provided which produces both a dialkyl carbonate and a diol with high productivity. In accordance with the present invention, the term "productivity" means the yield per unit volume of both the carbonation and transesterification zones per unit time, i.e. the space time yield for the overall integrated process.

The transesterification reaction may be represented by the following:

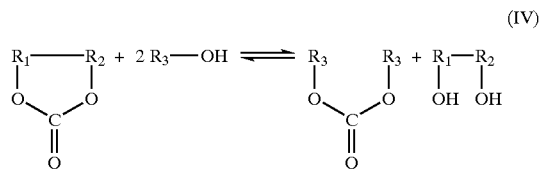

(IV)

wherein $R_1$ and $R_2$ in dependently of one another denote a divalent group represented by the formula —$(CH_2)_m$—, wherein m is an integer from 1 to 3, which is unsubstituted or substituted with at least one substituent selected from the group consisting of $C_1$–$C_{10}$ alkyl group and a $C_6$–$C_{10}$ aryl group, wherein $R_1$ and $R_2$ can share the same substituent; and $R_3$ is a monovalent aliphatic $C_1$–$C_{12}$ hydrocarbon group which is unsubstituted or substituted with at least one substituent selected from the group consisting of a $C_1$–$C_{10}$ alkyl group and a $C_6$–$C_{10}$ aryl group.

The reactants to the transesterification reaction (i.e. the cyclic carbonate and the aliphatic monohydric alcohol) are contacted in the presence of a transesterification catalyst. The transesterification catalyst can typically include any homogeneous or heterogeneous catalyst known in the art which provides adequate reaction kinetics and minimizes side reactions with the impurities contained in the cyclic carbonate.

Examples of such catalysts include alkali metals or alkaline earth metals, such as lithium, sodium, potassium, rubidium, cesium, magnesium, calcium, strontium, barium and the like; basic compounds such as hydrides, hydroxides, alkoxides, aryloxides and amides of alkali metals or alkaline earth metals and the like; basic compounds, such as carbonates and hydrogencarbonates of alkali metals or alkaline earth metal, alkali metal or alkaline earth metal salts of organic acids and the like; tertiary amines such as triethylamine, tributylamine, trihexylamine, benzyldiethylamine and the like; nitrogen-containing heteroaromatic compounds, such as N-alkylpyrrole, N-alkylindole, oxazole, N-alkylimidazole, N-alkylpyrazole, oxadiazole, pyridine, alkylpyridine, quinoline, alkylquinoline, isoquinoline, alkylisoquinoline, acridine, alkylacridine, phenanthroline, alkylphenanthroline, pyrimidine, alkylpyrimidine, pyradine, alkylpyradine, triazine, alkyltriazine and the like; cyclic amidines, such as diazabicycloundecene (DBU), diazabicyclononene (DBN) and the like; thallium compounds, such as thallium oxide, thalliun halides, thallium hydroxide, thallium carbonate, thallium nitrate, thallium sulfate, thallium salts of organic acids and the like; tin compounds, such as tributylmethoxytin, tributylethoxytin, dibutyldimethoxytin, diethyldiethoxytin, dibutyldiethoxytin, dibutylphenoxytin, diphenylmethoxytin, dibutyltin acetate, tributyltin chloride, tin 2-ethylhexanoate and the like; zinc compounds, such as dimethoxyzinc, diethoxyzinc, ethylenedioxyzinc, dibutoxyzinc and the like; aluminum compounds such as aluminum trimethoxide, aluminum triisopropoxide, aluminum tributoxide and the like; titanium compounds, such as tetramethoxytitanium, tetraethoxytitanium, tetrabutoxytitanium, dichlorodimethoxytitanium, tetraisopropoxytitanium, titanium acetate, titanium acetylacetonate and the like; phosphorus compounds, such as trimethylphosphine, triethylphosphine, tributylphosphine, triphenylphosphine, tributylmethylphosphonium halides, trioctylbutylphosphonium halides, triphenylmethylphosphonium halides and the like; zirconium compounds, such as zirconium halides, zirconocenes, zirconium acetylacetonate, zirconium alkoxides, zirconium acetate and the like; lead and lead-containing compounds, e.g., lead oxides, such as PbO, $PbO_2$, $Pb_3O_4$ and the like; lead sulfides, such as PbS, $Pb_2S_3$, $PbS_2$ and the like; lead hydroxides, such as $Pb(OH)_2$, $Pb_3O_2(OH)_2$, $Pb_2[PbO_2(OH)_2]$, $Pb_2O(OH)_2$ and the like; plumbites, such as $Na_2$, $PbO_2$, $K_2PbO_2$, $NaHPbO_2$, $KHPbO_2$ and the like; plumbates, such as $Na_2PbO_3$, $Na_2H_2PbO_4$, $K_2PbO_3$,$K_2[Pb(OH)_6]$, $K_4PbO4$, $Ca_2PbO_4$, $CaPbO_3$ and the like; lead carbonates and basic salts thereof, such as $PbCO_3$, $PbCO_3.Pb(OH)_2$ and the like; alkoxylead compounds and aryloxylead compounds, such as $Pb(OCH_3)_2$, $(CH_3O)Pb(OPh)$, $Pb(OPh)_2$ and the like; lead salts of organic acids, and carbonates and basic salts thereof, such as $Pb(OCOCH_3)_2$, $Pb(OCOCH_3)_4$, $Pb(OCOCH_3)_2.PbO.3H_2O$, and the like; organolead compounds, such as $Bu_4Pb$, $Ph_4Pb$, $Bu_3PbCl$, $Ph_3PbBr$, $Ph_3Pb$ (or $Ph_6Pb_2$), $Bu_3PbOH$, $Ph_2PbO$ and the like wherein Bu represents a butyl group and Ph represents a phenyl group; lead alloys, such as Pb—Na, Pb—Ca, Pb—Ba, Pb—Sn, Pb—Sb and the like; lead minerals, such as galena, zinc blende and the like; hydrates of these lead compounds; ion-exchangers, such as anion-exchange resins having teriary amino groups, amide groups, or at least one type of ion-exchange group selected from the group consisting of sulfonate, carbonxylate and phosphate groups; strongly basic solid anion-exchangers having quarternary ammonium groups as ion-exchange groups and the like; solid inorganic compounds, such as silica, silica-alumina, silica-magnesia, aluminosilicate, gallium silicate, various types of zeolites, various types of metal-exchanged zeolites, ammonium-exchanged zeolites; and the like.

Preferred homogeneous transesterification catalysts include alcoholates and alkali hydroxides and carbonates, such as sodium methylate and sodium hydroxide. Preferred heterogeneous transesterification catalysts include anion exchange resins having tertiary amine, quaternary ammonium, sulfonic acid or carboxylic acid functional groups or solid support catalysts containing alkaline earth metal halides such as those described in U.S. Pat. No. 5,498,743, which is incorporated herein by reference.

The specific catalyst is chosen to optimize the economics of the overall integrated process and will depend upon the particular cyclic carbonate and aliphatic monohydric alcohol reacted, the type and amount of impurities contained in the cyclic carbonate and the transesterification reaction conditions. For example, it is contemplated that sodium hydroxide and quaternary ammonium anion exchange resins, containing some carbonate or bicarbonate anions, are particularly effective as a transesterification catalyst for the synthesis of dimethyl carbonate and ethylene glycol in accordance with the present invention. The weight ratio of homogeneous catalyst to cyclic carbonate is typically about 0.0005:1 to 0.05:1, preferably about 0.002:1 to 0.01:1. In the case of a heterogeneous catalyst, the weight hourly space velocity (WHSV) will typically be from about 0.1 to about 10, preferably about 0.5 to about 2.

The transesterification reaction is preferably carried out in a continuous mode utilizing various reactor configurations, such as stirred-tank, tubular, fixed or packed-bed reactors, in a single or multiple-reactor configuration, a boiling pot surmounted by a trayed or packed column, or a reactive distillation column, at from about 50° C. up to about 250° C., preferably between about 75° C. up to about 140° C., and at pressures ranging from about atmospheric pressure up to about 14000 Kpa (2000 psi), preferably from about 140 Kpa (20 psi) up to about 2000 Kpa (300 psi). In the preferred mode of operation, the type of reactor, temperature and pressure are optimized to insure a relatively high conversion and selectivity to the desired dialkyl carbonate and diol and to optimize the economics of the overall integrated process. Generally, a reactive distillation column will tend to give higher conversions of ethylene carbonate and methanol, while a packed-bed reactor offers flexibility in handling various heterogeneous catalysts.

The effluent from the transesterification reaction will typically be fed to a series of separating apparatuses to recover the dialkyl carbonate and diol products. Examples of such separating apparatuses include a distillation type separating apparatus, an extractive distillation type separating apparatus, a liquid-liquid extraction type separating apparatus, a crystallization type separating apparatus, an absorption type separating apparatus and a membrane type separating apparatus. A combination of a plurality of different or identical separating apparatuses may be used. Among these separating apparatuses, a distillation type separating apparatus is especially preferred. The separated streams resulting from the use of the various separating apparatuses may also be subjected to further processing, such as additional reactions or incorporation into other chemical synthesis processes, as discussed more fully below.

One embodiment of the integrated process, which utilizes a homogeneous carbonation catalyst and a heterogeneous transesterification catalyst, is shown schematically in FIG. 1. Equipment not essential to the understanding of the invention such as heat exchangers, pumps, compressors and the like are not shown.

Referring now to FIG. 1, the carbonation reactor 1 is preferably a stirred tank reactor in which the alkylene oxide is reacted with $CO_2$ to form a cyclic carbonate. The reactor 1 is charged with alkylene oxide and catalyst via line 2 and with $CO_2$ via line 3. In the case of ethylene carbonate, the reaction of ethylene oxide and $CO_2$ is exothermic and the temperature of the reaction zone is usually maintained below about 220° C. and the pressure is maintained in the range from about 500 psia to about 1000 psia to enhance product quality. Preferably, the reaction temperature is between about 180° C. and 200° C. The molar ratio of $CO_2$ to ethylene oxide is generally maintained at about 1.3:1 to 1:1, preferably 1.15:1 to 1.05:1. Preferably, the effluent from reactor 1 is fed to a tubular polishing reactor 4, to obtain greater than 90% overall conversion of the alkylene oxide.

The carbonation reactor effluent is withdrawn from reactor 4 via line 5. The carbonation reactor effluent 5 contains cyclic carbonate, unreacted $CO_2$, a small amount of unreacted alkylene oxide, catalyst, and by-product impurities, such as mono-and poly-glycols. Also provided on reactor 1 is vent line 6 which can be operated continuously or intermittently to purge the reactor of volatile impurities which could unfavorably affect product quality. For example, in the case of ethylene carbonate synthesis from ethylene oxide and $CO_2$, acetaldehyde is formed which, if it remained in the reaction mixture, could initiate side reactions to form unwanted polymeric materials or other byproducts that could unfavorably affect product quality.

The carbonation reactor effluent is fed from line 5 into separator 7 from which $CO_2$ and unreacted alkylene oxide is separated as a gaseous effluent and returned to the carbonation reactor 1 via lines 8 and 3. A purge line 9 is also provided to vent some or all of the overhead gas from separator 7. Separator 7 is preferably a simple flash unit. In the case of ethylene carbonate the reactor effluent is flashed at pressures ranging from about 0.5 up to about 30 psia and temperatures between about 120 and 200° C. The liquid effluent will typically contain about 0.1 to 5 wt % catalyst, about 0.3 to 20 wt % polyglycols, about 0.2 to 20 wt % mono- ethylene glycol and about 90 to 99 wt % ethylene carbonate.

The liquid effluent from separator 7 is passed via line 10 to evaporator 11 from which a crude cyclic carbonate is recovered as a vaporous effluent which exits via line 12. In the case of ethylene carbonate, the operating conditions of the evaporator typically include temperatures in the range of about 120 to 180° C., under a vacuum in the range of about 10 to 80 mmHg. A liquid effluent from evaporator 11, which contains catalyst, glycols and other heavies, is recycled to the carbonation reactor via lines 13 and 2. A purge line 14 is also provided to prevent accumulation of glycols and other heavies. Optionally, evaporator 11 may be surmounted by a packed or trayed column rectifying section, having a condenser and reflux, as discussed above. In such a case, the crude cyclic carbonate is recovered overhead as a liquid. The crude cyclic carbonate thus recovered is generally not subjected to further distillation (or other purification) before being used as a transesterification feedstock. In another option, a second evaporator can be employed to recover additional cyclic carbonate and catalyst from the purge stream 14. Make-up catalyst is fed via lines 15 and 13 into line 2.

The crude cyclic carbonate, which contains mono- and poly-glycols in an amount of from about 0.5 to about 40 percent by weight of the total crude cyclic carbonate, is fed via line 12 into a transesterification reactor 16, which is preferably a fixed bed reactor. An aliphatic monohydric alcohol is also fed to the transesterification reactor 16 via line 17. The molar ratio of alcohol to cyclic carbonate fed to the reactor is generally from about 2:1 to about 6:1, preferably about 3:1 to about 4:1. In the case of dimethyl carbonate and ethylene glycol, the reaction of ethylene carbonate and methanol will be maintained at a temperature of about 80 to 200° C., preferably about 100 to 150° C., and pressures about 700 Kpa (100 psi) to 2000 Kpa (300 psi). The conversion per pass of ethylene carbonate to dimethyl carbonate is about 30 to 70%, preferably about 50 to 65%. The WHSV is generally about 0.3 to 3 $hr^{-1}$.

The transesterification reactor effluent is withdrawn from reactor 16 via line 18. The transesterification effluent 18 will typically contain dialkyl carbonate, a diol, unreacted cyclic carbonate, unreacted alcohol, and by-products such as organic oxygenates and polyglycols. For example, in the case of a transesterification reaction between ethylene carbonate and methanol to provide dimethyl carbonate and ethylene glycol, major by-products can include dimethyl ether, 2-methoxyethanol and di-and tri- ethylene glycols, with the reactor effluent typically containing about 10 to 30 wt % dimethyl carbonate, about 10 to 25 wt % ethylene glycol, about 10 to 25 wt % unreacted ethylene carbonate, about 30 to 60 wt % unreacted methanol, about 0.005 to 0.05 wt % dimethyl ether/2-methoxyethanol and about 0.01 to 0.1 wt % di- and tri-ethylene glycol. However, the composition, and byproduct yields in particular, can vary widely based upon the specific catalysts and operating conditions employed.

The transesterification reactor effluent is fed from line 18 into a distillation column 19, where an overhead product stream containing the dialkyl carbonate, alcohol and organic oxygenates is removed via line 20 and a bottoms product stream containing the diol, cyclic carbonate and polyglycols is removed via line 21. In the case of dimethyl carbonate and ethylene glycol, the distillation column is typically operated at a pressure of between about 5 and 30 psia and a temperature range at the top of the column of about 50 to 90° C. Optionally, a side-draw stream 22, which is depleted of the diol and cyclic carbonate, is withdrawn from column 19 and recycled to the transesterification reactor, to reduce the load on the dialkyl carbonate product distillation column 23.

The overhead product stream is fed via line 20 to a dialkyl carbonate product distillation column 23, where the alcohol is taken overhead and recycled via lines 24 and 17 to the transesterification reactor 16 and dialkyl carbonate product is removed from the bottom via line 26 and sent to storage. A purge stream 25 is also provided to prevent the accumulation of light byproduct impurities. In the case of dimethyl carbonate, the dialkyl carbonate product distillation column is typically operated at a pressure of about 120 psia to 200 psia and a temperature range of about 120 to 190° C. Dimethyl carbonate and methanol form a low-boiling azeotrope, so that the overhead stream includes up to about 15 wt %, and typically about 5–15 wt % dimethyl carbonate. This dimethyl carbonate is generally recycled to the transesterification reactor along with the methanol.

The bottoms product stream from distillation column 19 is fed via line 21 to a diol product distillation column 27, where the diol product is removed overhead via line 28 and sent to storage or further processing, and a bottoms stream containing cyclic carbonate, polyglycols and other heavies is removed via line 29. In the case of ethylene glycol, the distillation column is operated in a temperature range of about 100 to 170° C., under a vacuum in the range of about 200 to 50 mm Hg. The bottoms stream 29 is optionally recycled to the evaporator 11 via lines 30 and 10 and/or optionally recycled to the transesterification reactor 16 via lines 31 and 12. The recycle option will be chosen to optimize the economics of the process and will depend upon the specific dialkyl carbonate and diol being produced. If the bottoms stream 29 is entirely recycled to the transesterification reactor via lines 31 and 12, a purge stream 32 is provided to prevent an accumulation of polyglycols and other heavies.

In another embodiment, which utilizes a heterogeneous carbonation catalyst and a heterogeneous transesterification catalyst, reference will again be made to FIG. 1. In this embodiment the evaporator 11 of FIG. 1 is eliminated, so that the liquid effluent from separator 7 is passed from line 10 directly to line 12 and into the transesterification reactor 16. Lines 13, 14 and 15 are also eliminated, since there is no longer a recovery and recycle of a homogeneous carbonation catalyst. In addition, the bottoms stream 29 is recycled to the transesterification reactor 16 via lines 31 and 12 and a purge stream 32 is provided to prevent accumulation of polyglycols and other heavies.

In yet another embodiment, which utilizes a homogeneous transesterification catalyst, reference will again be made to FIG. 1. The bottoms stream 29 from the diol product distillation column 27, which contains homogeneous transesterification catalyst, unreacted cyclic carbonate, polyglycols and other heavies, will be recycled to the transesterification reactor via lines 31 and 12. A purge stream 32 is provided to prevent accumulation of polyglycols and other heavies. Optionally, an evaporator can be employed to recover additional unreacted cyclic carbonate and homogeneous transesterification catalyst from the purge stream 32. Make-up homogeneous transesterification catalyst is fed into line 12.

A hydrolysis reactor can also be incorporated into the integrated process to provide a highly purified diol, e.g. ethylene glycol. The feed to this hydrolysis reactor can include the diol product stream, which may contain small amounts of cyclic carbonate, and some or all of the unreacted cyclic carbonate containing stream, that is otherwise recycled to the transesterification reactor.

Use of the integrated process of the present invention for the production of dimethyl carbonate and ethylene glycol is particularly well suited for incorporation into an ethylene glycol plant, which produces ethylene glycol from ethylene, oxygen and water such as by the method described in the Encyclopedia of Chemical Processing and Design, J. J. MeKetta, Marcel Dekker, Inc., N.Y., P. 237 to 243 (1984), which is incorporated herein by reference. Typically, in such a process, ethylene is first reacted with oxygen in a selective oxidation reactor to produce ethylene oxide, $CO_2$ and water. The ethylene oxide and water is then fed to a hydration reactor to produce ethylene glycol and polyglycols.

A portion of the ethylene oxide produced in connection with such an ethylene glycol plant can be removed for use in connection with the present invention. The removed ethylene oxide can be returned as ethylene glycol, essentially on a 1:1 mole basis. Moreover, since the ethylene glycol produced in accordance with the present invention is primarily mono-ethylene glycol, the amount of ethylene oxide that becomes mono-ethylene glycol as opposed to polyethylene glycols is actually greater via the integrated process than by the ethylene glycol plant. As such, the ethylene glycol, having a higher percentage of mono-ethylene glycol, can be returned to the ethylene glycol plant just prior to the purification equipment, reducing the amount of glycol purification required for the volume returned. This is especially beneficial for the production of fibergrade mono-ethylene glycol, which has a minimum purity specification of 99.9 wt % mono-ethylene glycol.

Alternatively, excess ethylene oxide can be produced for use as a feed to the integrated process of the present invention. The $CO_2$ produced in the oxidation reaction of the ethylene glycol plant which is typically just vented to the atmosphere, can also be used as a feed to the integrated process.

EXAMPLES

The following examples have been carried out to illustrate preferred embodiments of the invention. These examples include reacting ethylene carbonate (EC) with methanol (MeOH) in the presence of an anionic resin catalyst and in the presence of a pseudoboehmite catalyst, respectively, and repeating the reactions over each catalyst after adding glycol impurities to the reactants to simulate the transesterification reaction of the integrated process.

Example 1

Dimethyl carbonate (DMC) and the ethylene glycol (EG) were prepared by reacting ethylene carbonate (EC) with methanol (MeOH) in the presence of an Amberlite IRA-68 anionic resin catalyst in a 300 ml autoclave reactor as follows: 7.1 grams of the IRA-68 catalyst were loaded into a 300 ml glass lined autoclave reactor with a Teflon®-coated stir bar. A feed containing 100 grams of a mixture of EC and MeOH, having a MeOH:EC molar ratio of 4:1, was added to the reactor. The reactor was maintained at 195° F. (91° C.) and 150 psig total pressure under constant mixing. After 3 hours the products were analyzed by standard GC techniques. The EC conversion was 38.4% with a DMC selectivity of 100.00% and an EG selectivity of 99.7%. The reaction conditions and results are listed in Table 1 below.

Example 2

Example 1 was repeated, except with the feed containing 0.4 grams of ethylene glycol (EG) and 1.3 grams of triethylene glycol (TEG). The EC conversion was 40.6% with a DMC selectivity of 99.6% and an EG selectivity of 96.3%. The reactor conditions and results are listed in Table 1 below.

Example 3

Example 1 was repeated, except with the feed containing 1.3 grams of EG and 4.0 grams of TEG. The EC conversion was 44.4% with a DMC selectivity of 99.7% and an EG selectivity of 99.1%. The reaction conditions and results are listed in Table 1 below.

Example 4

DMC and EG were prepared by reacting EC with MeOH in the presence of a pseudoboehmite (AlO—OH) catalyst in the 300 ml autoclave reactor employed in Example 1 as follows: 5.0 grams of the AlO—OH catalyst was loaded into the reactor. A feed containing 100 grams of a mixture of EC and MeOH, having a MeOH:EC molar ratio of 4:1, was added to the reactor. The reactor was maintained at 275° F. and 250 psig total pressure under constant mixing. After 4 hours, the products were analyzed by GC. The EC conversion was 23.9% with a DMC selectivity of 96.5% and an EG selectivity of 97.6%. The reaction conditions and results are listed in Table 1 below.

Example 5

Example 4 was repeated, except with the feed containing 0.4 grams of EG and 1.3 grams of TEG. The EC conversion was 27.7% with a DMC selectivity of 96.8% and an EG selectivity of 98.0%. The reaction conditions and results are listed in Table 1 below.

Example 6

Example 4 was repeated, except with the feed containing 1.3 grams of EG and 4.0 grams of TEG. The EC conversion was 25.1% with a DMC selectivity of 95.8% and an EG selectivity of 96.5%. The reaction conditions and results are listed in Table 1 below.

TABLE 1

Results of Experiments at Different Levels of Feed Impurities

| Example | 1 | 2 | 3 | 4 | 5 | 6 |
| --- | --- | --- | --- | --- | --- | --- |
| Catalyst Type | IRA-68 | IRA-68 | IRA-68 | AlO—OH | AlO—OH | AlO—OH |
| Cat. Wt. (gms) | 7.1 | 7.1 | 7.1 | 5.0 | 5.0 | 5.0 |
| Temp. (° F./° C.) | 195/91 | 195/91 | 195/91 | 275/135 | 275/135 | 275/135 |
| Press. (psig/Kpa) | 150/1034 | 150/1034 | 150/1034 | 250/1723 | 250/1723 | 250/1723 |
| Rxn Time (hrs.) | 3 | 3 | 3 | 4 | 4 | 4 |
| Feed Composition (wt %): | | | | | | |
| MeOH | 59.2 | 58.2 | 56.1 | 59.2 | 58.2 | 56.1 |
| EC | 40.8 | 40.1 | 38.7 | 40.8 | 40.1 | 38.7 |
| EG | 0.0 | 0.4 | 1.3 | 0.0 | 0.4 | 1.3 |
| TEG | 0.0 | 1.3 | 4.0 | 0.0 | 1.3 | 4.0 |
| MeOH/EC, Molar Ratio | 4.0 | 4.0 | 4.0 | 4.0 | 4.0 | 4.0 |
| Reaction Results: | | | | | | |
| EC Conv., % | 38.4 | 40.6 | 44.4 | 23.9 | 27.7 | 25.1 |
| DMC Selec., % | 100.0 | 99.6 | 99.7 | 96.5 | 96.8 | 95.8 |
| EG Selec., % | 99.7 | 96.3 | 99.1 | 97.6 | 98.0 | 96.5 |

A review of Table 1 reveals that high DMC yields can be obtained even with a glycol-contaminated EC feed. Thus, the purification steps typically employed in connection with a carbonation reaction to produce a high purity EC are not necessary in connection with the current integrated process of producing DMC and EG from EO, $CO_2$ and MeOH to achieve relatively high yields of the desired products.

We claim:

1. An integrated process for the production of a dialkyl carbonate and a diol from an alkylene oxide, carbon dioxide and an aliphatic monohydric alcohol comprising:
    (a) reacting an alkylene oxide with carbon dioxide in the presence of a carbonation catalyst in a first reaction zone to provide a crude cyclic carbonate stream comprising a cyclic carbonate and impurities;
    (b) directing said crude cyclic carbonate stream to a second reaction zone;
    (c) reacting said cyclic carbonate with an aliphatic monohydric alcohol, in said second reaction zone, in the presence of a transesterification catalyst to provide a crude product stream comprising a corresponding dialkyl carbonate and diol; and (d) recovering said dialkyl carbonate and said diol from said crude product stream.

2. The process of claim 1, wherein said alkylene oxide is of the formula:

wherein $R_1$ and $R_2$ independently of one another denote a divalent group represented by the formula —$(CH_2)_m$—, wherein m is an integer from 1 to 3, which is unsubstituted or substituted with at least one substituent selected from the group consisting of a $C_1$–$C_{10}$ alkyl group and a $C_6$–$C_{10}$ aryl group, wherein $R_1$ and $R_2$ can share the same substituent; and said aliphatic monohydric alcohol is of the formula:

wherein $R_3$ is a monovalent aliphatic $C_1$–$C_{12}$ hydrocarbon group which is unsubstituted or substituted with at least one substituent selected from the group consisting of a $C_1$–$C_{10}$ alkyl group and a $C_6$–$C_{10}$ aryl group.

3. The process of claim 1, wherein said carbonation catalyst is at least one catalyst selected from the group consisting of a solid catalyst and a homogeneous catalyst and said transesterification catalyst is at least one catalyst selected from the group consisting of a solid catalyst and a homogeneous catalyst.

4. The process of claim 1, wherein said impurities are present in an amount from about 0.5 to 40% by weight of the crude cyclic carbonate stream.

5. The process of claim 1, wherein said aliphatic monohydric alcohol contains dialkyl carbonate in an amount of up to about 15% by weight, based upon the total weight of said aliphatic monohydric alcohol and said dialkyl carbonate.

6. The process of claim 1, further comprising:
(i) separating unreacted aliphatic monohydric alcohol from said crude product stream, wherein said unreacted aliphatic monohydric alcohol contains dialkyl carbonate in an amount of up to about 15% by weight, based upon the total weight of said unreacted aliphatic monohydric alcohol and said dialkyl carbonate; and
(ii) recycling said unreacted aliphatic monohydric alcohol to the transesterification reaction of step (c).

7. The process of claim 1, further comprising:
(i) separating unreacted cyclic carbonate from said crude product stream, wherein said unreacted cyclic carbonate contains diols in an amount of up to about 40% by weight, based upon the total weight of said unreacted cyclic carbonate and said diols; and
(ii) recycling said unreacted cyclic carbonate to the transesterification reaction of step (c).

8. The process of claim 1, wherein said cyclic carbonate is ethylene carbonate, said aliphatic monohydric alcohol is methanol and said impurities comprise ethylene glycol and higher molecular weight glycols.

9. The process of claim 8, further comprising an upstream step of
(i) reacting ethylene with oxygen in a selective oxidation reaction zone to provide ethylene oxide for use in step (a); and a down stream step of
(ii) purifying the recovered diol from step (d).

10. The process of claim 1, wherein said carbonation catalyst is a homogeneous catalyst, said crude cyclic carbonate stream from step (a) further comprises said homogeneous catalyst and said process further comprises, upstream of step (b), the steps of:
(i) separating said crude cyclic carbonate stream of step (a) using an apparatus selected from the group consisting of a conventional evaporator and an evaporator surmounted by a rectifying column, to provide a homogeneous catalyst stream and a crude cyclic carbonate stream, depleted of said homogeneous catalyst; and
(ii) recycling at least a portion of said homogeneous catalyst stream to the carbonation reaction of step (a).

11. The process according to claim 1, where in said recovering of said dialkyl carbonate and said diol from said crude product stream further comprises:
(a) concentration of impurities from said crude product stream to form a bottoms stream; and
(b) recycling at least a portion of said bottoms stream to said crude cyclic carbonate stream.

12. A process for the production of a dialkyl carbonate and a diol from an alkylene oxide, carbon dioxide and an aliphatic monohydric alcohol comprising:
(a) reacting an alkylene oxide with carbon dioxide in the presence of a carbonation catalyst in a first reaction zone to provide a crude cyclic carbonate stream comprising a cyclic carbonate and impurities;
(b) directing said crude cyclic carbonate stream to a second reaction zone;
(c) reacting said cyclic carbonate with an aliphatic monohydric alcohol, in said second reaction zone, in the presence of a transesterification catalyst to provide a crude product stream comprising a corresponding dialkyl carbonate and diol; and
(d) recovering said dialkyl carbonate and said diol from said crude product stream.

* * * * *